US008846607B2

(12) United States Patent
Edwards et al.

(10) Patent No.: US 8,846,607 B2
(45) Date of Patent: Sep. 30, 2014

(54) PARTICLES FOR TREATMENT OF PULMONARY INFECTION

(75) Inventors: David A. Edwards, Boston, MA (US); Jennifer Fiegel, Arlington, MA (US); Jean Sung, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 816 days.

(21) Appl. No.: 11/720,595

(22) PCT Filed: Oct. 19, 2005

(86) PCT No.: PCT/US2005/037484
§ 371 (c)(1),
(2), (4) Date: May 31, 2007

(87) PCT Pub. No.: WO2007/011396
PCT Pub. Date: Jan. 25, 2007

(65) Prior Publication Data
US 2008/0213373 A1 Sep. 4, 2008

Related U.S. Application Data

(60) Provisional application No. 60/623,738, filed on Oct. 29, 2004.

(51) Int. Cl.
*A61K 9/14* (2006.01)
*A61P 31/06* (2006.01)
*A61P 11/00* (2006.01)
*A61K 38/12* (2006.01)
*A61K 9/00* (2006.01)
*A61K 9/16* (2006.01)

(52) U.S. Cl.
CPC ............. *A61K 9/0075* (2013.01); *A61K 9/1617* (2013.01); *A61K 9/1694* (2013.01); *Y10S 514/924* (2013.01)
USPC ............... 514/2.4; 514/1.5; 514/924; 530/317

(58) Field of Classification Search
None
See application file for complete search history.

(56) References Cited

U.S. PATENT DOCUMENTS

| 4,069,819 | A |   | 1/1978  | Valentini et al. |       |
|-----------|---|---|---------|------------------|-------|
| 4,995,385 | A |   | 2/1991  | Valentini et al. |       |
| 5,192,528 | A | * | 3/1993  | Radhakrishnan et al. | 424/45 |
| 5,814,617 | A |   | 9/1998  | Hoffman et al.   |       |
| 5,855,913 | A |   | 1/1999  | Hanes et al.     |       |
| 5,962,566 | A |   | 10/1999 | Grandfils et al. |       |
| 5,985,309 | A |   | 11/1999 | Edwards et al.   |       |
| 5,997,848 | A |   | 12/1999 | Patton et al.    |       |
| 6,117,454 | A |   | 9/2000  | Kreuter et al.   |       |
| 6,143,211 | A |   | 11/2000 | Mathiowitz et al. |      |
| 6,517,860 | B1 |  | 2/2003  | Roser et al.     |       |
| 6,518,239 | B1 |  | 2/2003  | Kuo et al.       |       |
| 6,586,008 | B1 |  | 7/2003  | Batycky et al.   |       |
| 6,766,799 | B2 |  | 7/2004  | Edwards et al.   |       |
| 2002/0052310 | A1 | | 5/2002 | Edwards et al.   |       |
| 2003/0059471 | A1 | * | 3/2003 | Compton et al.  | 424/489 |
| 2003/0166509 | A1 | * | 9/2003 | Edwards et al.  | 514/3 |
| 2003/0232020 | A1 | | 12/2003 | York et al.     |       |
| 2004/0105821 | A1 | | 6/2004 | Bernstein et al. |       |

FOREIGN PATENT DOCUMENTS

| WO | WO 95/00128 |    | 1/1995 |
|----|-------------|----|--------|
| WO | WO 03/043586 |   | 5/2003 |
| WO | WO 2004024213 | A2 * | 3/2004 |
| WO | WO 2004/069253 | | 8/2004 |

OTHER PUBLICATIONS

Finlay, WH; Stapleton, KW; Zuberbuhler, P; "Fine Particle Fraction as a Measure of Mass Depositing in the Lung During Inhalation of Nearly Isotonic Nebulized Aerosols", J. Aerosol Sci., vol. 28(7), 1997, pp. 1301-1309.*

Figel et al. "Preparation and in Vivo Evaluation of a Dry Powder for Inhalation of Capreomycin", Pharmaceutical Research, vol. 25(4), Apr. 2008, pp. 805-811.*

Bosquillon, et al., "Influence of formulation excipients and physical characteristics of inhalation dry powders on their aerosolization performance", *J. Control Release*, 70(3):329-39 (2001).

(Continued)

*Primary Examiner* — Ernst V Arnold
(74) *Attorney, Agent, or Firm* — Pabst Patent Group LLP

(57) ABSTRACT

Formulations have been developed to treat or reduce the spread of respiratory infections, especially chronic or drug resistant infections, particularly tuberculosis (TB), severe acute respiratory syndrome (SARS), meningococcal meningitis, Respiratory syncytial virus (RSV), influenza, and small pox. Formulations include a drug or vaccine in the form of a microparticle, nanoparticle, or aggregate of nanoparticles, and, optionally, a carrier, which can be delivered by inhalation. Giving the drugs via an inhaler sidesteps the problems associated with oral or injectable drugs by bypassing the stomach and liver, and delivering the medication directly into the lungs. In one embodiment, the particle containing the agent is a large porous aerosol particle (LPPs). In another embodiment, the particles are nanoparticles, which can be administered as porous nanoparticle aggregates with micron diameters that disperse into nanoparticles following administration. Optionally, the nanoparticles are coated, such as with a surfactant or protein coating. The formulation may be administered as a powder or administered as a solution or via an enteral or non-pulmonary parenteral route of administration. The formulation is preferably administered as a pulmonary formulation. In the preferred embodiment for treatment of TB, the vaccine is a BCG vaccine that is stable at room temperature, or is an antibiotic effective against TB, such as capreomycin or PA-824, loaded at a very high percentage into the microparticles or nanoparticles. In one embodiment, a patient is treated with formulations delivering both antibiotic and vaccine.

**14 Claims, 1

(56) References Cited

OTHER PUBLICATIONS

Amnoury, et al., "In vitro release kinetic pattern of indomethacin from poly (d,l-lactic) nanocapsules", *J. Pharm. Sci.*, 79:763-767 (1990).

Bazile, et al., "Body distribution of fully biodegradable [$^{14}$C]-poly(lactic acid) nanoparticles coated with albumin after parenteral administration to rats", *Biomaterials*, 13(15):1093-1102 (1992).

Chen, et al. "Preparation of cyclosporine A nanoparticles by evaporative precipitation into aqueous solution", *Int. J. Pharm.*, 24:3-14 (2002).

Dalencon, et al, "Atovaquone and rifabutine-loaded nanocapsules: formulation studies", *Int. J. of Pharm.*, 153:127-130 (1997).

Gonda, "Aerosols for delivery of therapeutic and diagnostic agents to the respiratory tract," *Critical Reviews in Therapeutic Drug Carrier Systems*, 6:273-313 (1990).

Gref, et al., "Biodegradable long-circulating polymeric nanospheres", *Science*, 263:1600-1603 (1994).

Heifets, et al., "Capreomycin is active against non-replicating *M. tuberculosis*", *Ann. Clin. Microbiol. Antimicrobiol.* 4:6 (2005).

Julienne, et al., *Proceed. Intern. Symp. Control. Rel. Bioact. Mater.*, pp. 77-78 (1989).

Kawaguchi, et al., "Phagocytosis of latex particles by leucocytes. I. Dependence of phagocytosis on the size and surface potential of particles", *Biomaterials*, 7:61-66 (1986).

Krenis and Strauss, "Effect of size and concentration of latex particles on respiration of human blood leucocytes" *Proc. Soc. Exp. Med.*, 107:748-750 (1961).

Le Roy Boehm, et al, "Poly epsilon-caprolactone nanoparticles containing a poorly soluble pesticide: formulation and stability study", *J. Microencapsulation*, 17:195-205 (2000).

Lee, et al., "Preparation of Aromatic Polycarbonate Nanoparticles using Supercritical Carbon Dioxide", *J. of Nan. Res.*, 4(1-2):53-59 (2002).

Rudt and Muller, "In vitro phagocytosis assay of nano- and microparticles by chemiluminescence. 1. Effect of analytical parameters, particle size and particle concentration", *J. Contr. Rel.*, 22:263-271 (1992).

Snyder, et al., "Characterization of microorganisms by thermogravimetric analysis—mass spectrometry" *Analytica Chimica Acta*, 536(1-2):283-293 (2005).

Jung, et al., "Tetanus toxoid loaded nanoparticles from sulfobutylated poly(vinylalcohol)-graft-poly(lactide-co-glycolide): Evaluation of antibody response after oral and nasal application in mice," *Pharmaceutical Research*, 18(3): 352-360 (2001).

* cited by examiner

PARTICLES FOR TREATMENT OF PULMONARY INFECTION

This application is a 371 application of PCT/US2005/037484 filed Oct. 19, 2005, which claims priority to U.S. Ser. No. 60/623,738 filed Oct. 29, 2004.

The United States government has rights to this invention by virtue of NIH grant number 5 U01 AI61336-02 from the National Institute of Allergy and Infectious Diseases.

BACKGROUND OF THE INVENTION

TB, or tuberculosis, is a disease caused by bacteria called *Mycobacterium tuberculosis*. The bacteria can attack any part of the body, but usually attack the lungs. TB disease was once the leading cause of death in the United States. In the 1940s, scientists discovered the first of several drugs now used to treat TB. As a result, TB slowly began to disappear in the United States. However, drug resistant strains and infection of compromised patients has resulted in an increase in TB. Between 1985 and 1992, the number of TB cases increased; more than 16,000 cases were reported in 2000 in the United States. TB claims about 2 million lives every year. India, China, and Africa are hot spots, and the disease is increasing at a worrisome rate in Eastern Europe and nations that were formerly members of the Soviet Union.

TB is spread through the air from one person to another. The bacteria are put into the air when a person with TB disease of the lungs or throat coughs or sneezes. People nearby may breathe in these bacteria and become infected.

When a person breathes in TB bacteria, the bacteria can settle in the lungs and begin to grow. From there, they can move through the blood to other parts of the body, such as the kidney, spine, and brain. TB in the lungs or throat can be infectious. This means that the bacteria can be spread to other people. TB in other parts of the body, such as the kidney or spine, is usually not infectious. People with TB disease are most likely to spread it to people they spend time with every day. This includes family members, friends, and coworkers. People who are infected with latent TB do not feel sick, do not have any symptoms, and cannot spread TB, but they may develop TB disease at some time in the future. People with TB disease can be treated and cured if they seek medical help. Even better, people who have latent TB infection but are not yet sick can take medicine so that they will never develop TB disease.

Vaccination against TB currently involves needle injection of Bacille Camette-Guerin (BCG). This vaccine needs to refrigerated prior to delivery. However refrigeration is not always available, especially in developing countries. Lyophilization may be used to prepare a vaccine that is stable at room-temperature, if the molecule is not denatured during this procedure. However, when BCG is lyophilized most of its activity is lost. Therefore there is a need for a method for making a more stable vaccine for TB.

Currently drugs and vaccines for the treatment or prevention of TB are delivered to patients orally or by needle injections. A less painful and simpler method for delivering drugs and vaccines is needed. Getting patients to take a full course of drugs looms as one of the big problems in eradicating TB. After two to three months of treatment, the patients feel better, then they stop taking their medications. But they need six months of therapy to cure the disease. Drugs given by injection are painful and have toxic side effects. Pills are easier to take, but they, too, can cause liver and stomach problems including nausea, diarrhea, and vomiting.

There are several other major respiratory infectious diseases that suffer from the same deficiencies in treatment, including severe acute respiratory syndrome (SARS), meningococcal meningitis, influenza, Respiratory syncytial virus and small pox.

It is therefore an object of the invention to provide improved methods and formulations for use in decreasing or limiting the spread of tuberculosis and other infectious respiratory diseases.

It is another object of the invention to provide improved formulations for the treatment of tuberculosis and other infectious respiratory diseases which do not have to be injected.

It is another object of the invention to provide a more stable vaccine for TB and other infectious respiratory diseases and methods for making the vaccine.

SUMMARY OF THE INVENTION

Formulations have been developed to treat or reduce the spread of respiratory infections, especially chronic or drug resistant infections, particularly tuberculosis (TB), severe acute respiratory syndrome (SARS), meningococcal meningitis, Respiratory syncytial virus (RSV), influenza, and small pox.

Formulations include a drug or vaccine in the form of a microparticle, nanoparticle, or aggregate of nanoparticles, and, optionally, a carrier, which can be delivered by inhalation. Giving the drugs via an inhaler sidesteps the problems associated with oral or injectable drugs by bypassing the stomach and liver, and delivering the medication directly into the lungs. In one embodiment, the particle containing the agent is a large porous aerosol particle (LPPs). In another embodiment, the particles are nanoparticles, which can be administered as porous nanoparticle aggregates with micron diameters that disperse into nanoparticles following administration. Optionally, the nanoparticles are coated, such as with a surfactant or protein coating. The formulation may be administered as a powder or administered as a solution or via an enteral or non-pulmonary parenteral route of administration. The formulation is preferably administered as a pulmonary formulation.

In the preferred embodiment for treatment of TB, the vaccine is a BCG vaccine that is stable at room temperature, or is an antibiotic effective against TB, such as capreomycin or PA-824, loaded at a very high percentage into the microparticles or nanoparticles, preferably at least 50 wt %, more preferably at least 80 wt %. In one embodiment, a patient is treated with formulations delivering both antibiotic and vaccine.

The example demonstrates preparation and analysis of an inhalable capreomycin porous particle, having a diameter of about 4.2 microns, and nanometer thick walls, having excellent aerodynamic properties, drug loading and stability.

DETAILED DESCRIPTION OF THE INVENTION

I. Particle Formulations

Figure 1A:
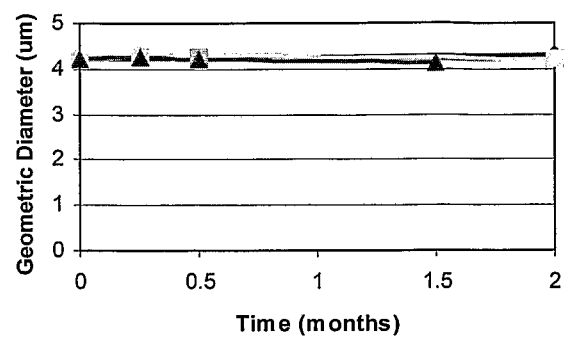
FIGS. 1A, 1B and 1C are graphs of time-dependant stability of (A) geometric diameter, (B) fine particle fraction ($FPF_{TD}$)<5.8 um of particles, and (C) capreomycin content of an aerosol powder initially containing 80% capreomycin, stored under various stress conditions. Legend key: ▲ 4° C.; ■ RT dark; ■ RT light; ▲ 40° C./75% RH closed; * 40° C./75% RH open.

The formulations include particles of drug and, optionally, excipient, optional excipient or pharmaceutical carrier. The formulations can be nanoparticles, microparticles, or microaggregates of nanoparticles. The aggregates can be coated. The formulations can be in the form of a powder for inhalation, or dispersed in a solution or encapsulated for delivery via a route other than pulmonary, such as nasal, buccal, oral, or injection, although pulmonary is preferred.

Particles, Nanoparticles and Aggregates of Nanoparticles

Particles are preferably formed of drug to be delivered in combination with excipient by spray drying a solution of drug and excipient. The spray drying conditions determine the size of the particles, as well as the density. The size and density determine whether the particle is inhaled into the lung. The diameter of particles in a sample depend upon factors such as particle composition and methods of synthesis. The distribution of size of particles or aggregates in a sample can be selected to permit optimal deposition within targeted sites within the respiratory tract. An $FPF_{TD}$<3.3 μm represents the percentage of aerosols that should deposit in the lower respiratory tract, whereas an $FPF_{TD}$<5.8 μm represents the percentage of aerosols that should deposit in the middle to lower respiratory tract. Unless stated otherwise, the particles or aggregates described herein will have an $FPF_{TD}$<5.8 μm.

In a preferred embodiment, the particle or particle aggregates are aerodynamically light, having a preferred size, e.g., a volume median geometric diameter (VMGD or geometric diameter) of at least about 5 microns. In another embodiment, the VMGD is from about 5 microns to about 15 microns. The particles in the example below have a diameter of about 4.2 microns. In another embodiment, the particles have a VMGD ranging from about 10 μm to about 15 μm, and as such, more successfully avoid phagocytic engulfment by alveolar macrophages and clearance from the lungs, due to size exclusion of the particles from the phagocytes' cytosolic space. Phagocytosis of particles by alveolar macrophages decreases precipitously as particle diameter increases beyond about 3 μm and less than about 1 μm (Kawaguchi et al., Biomaterials 7: 61-66, 1986; Krenis and Strauss, Proc. Soc. Exp. Med., 107: 748-750, 1961; and Rudt and Muller, J. Contr. Rel., 22: 263-272, 1992). In other embodiments, the aggregates have a median diameter (MD), MMD, a mass median envelope diameter (MMED) or a mass median geometric diameter (MMGD) of at least 5 μm, for example from about 5 μm to about 30 μm.

The nanoparticles contained within the aggregates have a geometric diameter of approximately less than about 1 μm, for example, from about 25 nanometers to approximately 1 μm. Such geometric diameters are small enough that they escape clearance from the body by macrophages, and can reside in the body for long periods of time.

Suitable particles or aggregates can be fabricated or separated, for example, by filtration or centrifugation, to provide a particle sample with a preselected size distribution. For example, greater than about 30%, 50%, 70%, or 80% of the particles or aggregates in a sample can have a diameter within a selected range of at least about 5 μm. The selected range within which a certain percentage of the particles or aggregates must fall may be, for example, between about 5 and about 30 μm, or optimally between about 5 and about 25 μm. In one preferred embodiment, at least a portion of the particles or aggregates have a diameter between about 5 μm and about 15 μm. Optionally, the particle sample also can be fabricated wherein at least about 90%, or optionally about 95% or about 99%, have a diameter within the selected range.

The diameter of the particles or aggregates, for example, their VMGD, can be measured using an electrical zone sensing instrument such as a Multisizer IIe, (Coulter Electronic, Luton, Beds, England), or a laser diffraction instrument (for example, Helos, manufactured by Sympatec, Princeton, N.J.) or by SEM visualization. Other instruments for measuring particle diameter are well known in the art. Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid impinger (MSLI).

The aerodynamic diameter, $d_{aer}$, can be calculated from the equation:

$$d_{aer}=d_g\sqrt{\rho_{tap}}$$

where $d_g$ is the geometric diameter, for example the MMGD and ρ is the particle mass density approximated by the powder tap density.

Particles are preferably formed using spray drying techniques. In such techniques, a spray drying mixture, also referred to herein as "feed solution" or "feed mixture," is formed to include nanoparticles comprising a bioactive agent and, optionally, one or more additives that are fed to a spray dryer.

Spray drying is a standard process used in the food, pharmaceutical, and agricultural industries. In spray drying, moisture is evaporated from an atomized feed (spray) by mixing sprayed droplets with a drying medium (e.g., air or nitrogen). This process dries the droplets of their volatile substance and leaves non-volatile components of "dry" particles that are of a size, morphology, density, and volatile content controlled by the drying process. The mixture being sprayed can be a solvent, emulsion, suspension, or dispersion. Many factors of the drying process can affect the properties of the dry particles, including the type of nozzle, drum size, flow rate of the volatile solution and circulating gas, and environmental conditions (Sacchetti and Van Oort, *Spray Drying and Supercritical Fluid Particle Generation Techniques*, Glaxo Wellcome Inc., 1996).

Typically, the process of spray drying involves four processes, dispersion of a mixture in small droplets, mixing of the spray and a drying medium (e.g., air), evaporation of moisture from the spray, and separation of the dry product from the drying medium (Sacchetti and Van Oort, *Spray Drying and Supercritical Fluid Particle Generation Techniques*, Glaxo Wellcome Inc., 1996).

The dispersion of the mixture in small droplets greatly increases the surface area of the volume to be dried, resulting in a more rapid drying process. Typically, a higher energy of dispersion leads to smaller droplets obtained. The dispersion can be accomplished by any means known in the art, including pressure nozzles, two-fluid nozzles, rotary atomizers, and ultrasonic nozzles (Hinds, *Aerosol Technology*, $2^{nd}$ Edition, New York, John Wiley and Sons, 1999).

Following the dispersion (spraying) of the mixture, the resultant spray is mixed with a drying medium (e.g., air). Typically, the mixing occurs in a continuous flow of heated air. The hot air improves heat transfer to the spray droplets and increases the rate of evaporation. The air stream can either be exhausted to the atmosphere following drying or recycled and reused. Air flow is typically maintained by providing positive and/or negative pressure at either end of the stream (Sacchetti and Van Oort, *Spray Drying and Supercritical Fluid Particle Generation Techniques*, Glaxo Wellcome Inc., 1996).

When the droplets come into contact with the drying medium, evaporation takes place rapidly due to the high specific surface area and small size of the droplets. Based on the properties of the drying system, a residual level of moisture may be retained within the dried product (Hinds, *Aerosol Technology*, 2$^{nd}$ Edition, New York, John Wiley and Sons, 1999).

The product is then separated from the drying medium. Typically, primary separation of the product takes place at the base of the drying chamber, and the product is then recovered using, e.g., a cyclone, electrostatic precipitator, filter, or scrubber (Masters et al., *Spray Drying Handbook*. Harlow, UK, Longman Scientific and Technical, 1991).

The properties of the final product, including particle size, final humidity, and yield depend on many factors of the drying process. Typically, parameters such as the inlet temperature, air flow rate, flow rate of liquid feed, droplet size, and mixture concentration are adjusted to create the desired product (Masters et al., *Spray Drying Handbook*, Harlow, UK, Longman Scientific and Technical, 1991).

The inlet temperature refers to the temperature of the heated drying medium, typically air, as measured prior to flowing into the drying chamber. Typically, the inlet temperature can be adjusted as desired. The temperature of the drying medium at the product recovery site is referred to as the outlet temperature, and is dependent on the inlet temperature, drying medium flow rate, and properties of the sprayed mixture. Typically, higher inlet temperatures provide a reduction in the amount of moisture in the final product (Sacchetti and Van Oort, *Spray Drying and Supercritical Fluid Particle Generation Techniques*, Glaxo Wellcome Inc., 1996).

The air flow rate refers to the flow of the drying medium through the system. The air flow can be provided by maintaining positive and/or negative pressure at either end or within the spray drying system. Typically, higher air flow rates lead to a shorter residence time of the particles in the drying device (i.e., the drying time) and lead to a greater amount of residual moisture in the final product (Masters et al., *Spray Drying Handbook*, Harlow, UK, Longman Scientific and Technical, 1991).

The flow rate of the liquid feed refers to the quantity of liquid delivered to the drying chamber per unit time. The higher the throughput of the liquid, the more energy is needed to evaporate the droplets to particles. Thus, higher flow rates lead to lower output temperatures. Typically, reducing the flow rate while holding the inlet temperature and air flow rate constant reduces the moisture content of the final product (Masters et al., *Spray Drying Handbook*, Harlow, UK, Longman Scientific and Technical, 1991).

The droplet size refers to the size of the droplets dispersed by the spray nozzle. Typically, smaller droplets provide lower moisture content in the final product with smaller particle sizes (Hinds, *Aerosol Technology*, 2$^{nd}$ Edition, New York, John Wiley and Sons, 1999).

The concentration of the mixture to be spray dried also influences the final product. Typically, higher concentrations lead to larger particle sizes of the final product, since there is more material per sprayed droplet (Sacchetti and Van Oort, *Spray Drying and Supercritical Fluid Particle Generation Techniques*, Glaxo Wellcome Inc., 1996).

Systems for spray drying are commercially available, for example, from Armfield, Inc. (Jackson, N.J.), Brinkmann Instruments (Westbury, N.Y.), BUCHI Analytical (New Castle, Del.), Niro Inc (Columbia, Md.), Sono-Tek Corporation (Milton, N.Y.), Spray Drying Systems, Inc. (Randallstown, Md.), and Labplant, Inc. (North Yorkshire, England).

The final moisture content of the spray dried powder can be determined by any means known in the art, for example, by thermogravimetric analysis. The moisture content is determined by thermogravimetric analysis by heating the powder, and measuring the mass lost during evaporation of moisture (Maa et al., *Pharm. Res.*, 15:5, 1998). Typically, for a sample that contains cellular material (e.g., bacteria), the water will be evaporated in two phases. The first phase, referred to as free water, is primarily the water content of the dry excipient. The second phase, referred to as bound water, is primarily the water content of the cellular material. Both the free and bound water can be measured to determine if the powder contains a desired moisture content in either the excipient or cellular material (Snyder et al., *Analytica Chimica Acta*, 536:283-293, 2005).

The spray dryer used to form the particle can employ a centrifugal atomization assembly, which includes a rotating disk or wheel to break the fluid into droplets, for example, a 24 vaned atomizer or a 4 vaned atomizer. The rotating disk typically operates within the range from about 1,000 to about 55,000 rotations per minute (rpm).

Alternatively, hydraulic pressure nozzle atomization, two fluid pneumatic atomization, sonic atomization or other atomizing techniques, as known in the art, also can be employed. Commercially available spray dryers from suppliers such as Niro, APV Systems, Denmark, (e.g., the APV Anhydro Model) and Swenson, Harvey, Ill., as well as scaled-up spray dryers suitable for industrial capacity production lines can be employed, to generate the particles as described herein. Commercially available spray dryers generally have water evaporation capacities ranging from about 1 to about 120 kg/hr. For example, a Niro Mobile Minor® spray dryer has a water evaporation capacity of about 7 kg/hr. The spray driers have a 2 fluid external mixing nozzle, or a 2 fluid internal mixing nozzle (e.g., a NIRO Atomizer Portable spray dryer).

Suitable spray-drying techniques are described, for example, by K. Masters in "Spray Drying Handbook," John Wiley & Sons, New York, 1984. Generally, during spray-drying, heat from a hot gas such as heated air or nitrogen is used to evaporate the solvent from droplets formed by atomizing a continuous liquid feed. Other spray-drying techniques are well known to those skilled in the art. In a preferred embodiment, a rotary atomizer is employed. An example of a suitable spray dryer using rotary atomization includes the Mobile Minor® spray dryer, manufactured by Niro, Denmark. The hot gas can be, for example, air, nitrogen or argon.

Preferably, the particles are obtained by spray drying using an inlet temperature between about 90° C. and about 400° C. and an outlet temperature between about 40° C. and about 130° C.

Suitable organic solvents that can be present in the mixture to be spray dried include, but are not limited to, alcohols, for example, ethanol, methanol, propanol, isopropanol, butanols, and others. Other organic solvents include, but are not limited to, perfluorocarbons, dichloromethane, chloroform, ether, ethyl acetate, methyl tert-butyl ether and others. Another example of an organic solvent is acetone. Aqueous solvents that can be present in the feed mixture include water and buffered solutions. Both organic and aqueous solvents can be present in the spray-drying mixture fed to the spray dryer. In one embodiment, an ethanol water solvent is preferred with the ethanol:water ratio ranging from about 20:80 to about 90:10. The mixture can have an acidic or an alkaline pH. Optionally, a pH buffer can be included. Preferably, the pH can range from about 3 to about 10. In another embodiment, the pH ranges from about 1 to about 13.

The total amount of solvent or solvents employed in the mixture being spray dried generally is greater than about 97 weight percent. Preferably, the total amount of solvent or solvents employed in the mixture being spray dried generally is greater than about 99 weight percent The amount of solids (nanoparticles containing bioactive agent, additives, and other ingredients) present in the mixture being spray dried generally is less than about 3.0 weight percent. Preferably, the amount of solids in the mixture being spray dried ranges from about 0.05% to about 1.0% by weight.

Pharmaceutically Active Agents

Agents to be delivered include therapeutic, prophylactic and/or diagnostic agents (collectively, "bioactive agents") for treatment of respiratory infectious diseases such as TB, severe acute respiratory syndrome (SARS), influenza, and small pox. Suitable bioactive agents include agents that can act locally, systemically or a combination thereof. The term "bioactive agent," as used herein, is an agent, or its pharmaceutically acceptable salt, which when released in vivo, possesses the desired biological activity, for example therapeutic, diagnostic and/or prophylactic properties in vivo. Examples of bioactive agents include, but are not limited to, synthetic inorganic and organic compounds, proteins, peptides, polypeptides, DNA and RNA nucleic acid sequences or any combination or mimic thereof, having therapeutic, prophylactic or diagnostic activities. Compounds with a wide range of molecular weight can be used, for example, compounds with weights between 100 and 500,000 grams or more per mole.

In one preferred embodiment, the bioactive agent is an antibiotic for treatment of a respiratory infection such as tuberculosis, such as capreomycin, PA-824, rifapicin, rifapentine, and quinolones (e.g. Moxifloxacin (BAY 12-8039), aparfloxacin, gatifloxacin, CS-940, Du-6859a, sitafloxacin, HSR-903, levofloxacin, WQ-3034), ciprofloxacin, and levofloxacin. Capreomycin is a relatively hydrophilic antibiotic molecule. It is currently used as a second-line defense molecule, in the prevention of TB. Capreomycin shows a one to two log decrease in colony forming units ("CFU") after one month against non-replicating TB in vitro, so there is potential for latent TB treatment, as reported by Heifets, et al. Ann. Clin. Microbiol. Antimicrobiol. 4(6) (2005). PA-824 is a bactericidal antibiotic which targets a flavenoid F420 and also prevents mycolic acid synthesis and lipid biosynthesis. Rifapentine inhibits RNA polymerase by binding to the β subunit of the protein and acts as a bactericidal antibiotic.

In another preferred embodiment, the bioactive agent is a vaccine, such as a BCG vaccine, which is effective against TB, or flu antigens.

For treatment of viral respiratory infections, the bioactive agent is preferably an antiviral alone or in combination with vaccine. Four antiviral medications are commonly prescribed for the A category of influenza viruses, amantadin, rimantadine, zanamavir and the widely-stockpiled oseltamivir. These are neuraminidase inhibitors, which block the virus from replicating. If taken within a couple of days of the onset of illness, they can ease the severity of some symptoms and reduce the duration of sickness.

Multi-drug resistant tuberculosis (MDR-TB) is emerging as a significant public health threat, creating an unmet medical need that requires the development of new treatment approaches. In a preferred embodiment very high drug doses are delivered to the site of primary infection for rapid sterilization of the lung mucosa and reduction in the duration of MDR-TB therapy. The formulation for treatment of drug resistant forms of infection may include very high loading of one or more antibiotics or a combination of antibiotic and vaccine.

The nanoparticles can contain up to about 100% (w/w) bioactive agent. In the preferred embodiment, the particles contain at least 50.00%, 60.00%, 75.00%, 80.00%, 85.00%, 90.00%, 95.00%, 99.00% or more, of bioactive agent (dry weight of composition). In the case of capreomycin and other similar drugs, the preferred dosage loading is at least 50 wt %, more preferably 80 wt %. The amount of bioactive agent used will vary depending upon the desired effect, the planned release levels, and the time span over which the bioactive agent will be released.

Excipients and Pharmaceutically Acceptable Carriers

As used herein, an additive is any substance that is added to another substance to produce a desired effect in, or in combination with, the primary substance. As generally used herein, an "excipient" means a compound that is added to a pharmaceutical formulation in order to confer a suitable consistency. For example, the particles can include a surfactant. As generally used herein, the term "surfactant" refers to any agent which preferentially absorbs to an interface between two immiscible phases, such as the interface between water and an organic polymer solution, a water/air interface, a water/oil interface, a water/organic solvent interface or an organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

The particles and components thereof can be drug, drug and excipient, or drug in a polymer, which can be biodegradable or nonbiodegradable, or a material such as silica, sterols such as cholesterol, stigmasterol, .beta.-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof, spingomyelins such as stearyl, palmitoyl, and tricosanyl spingomyelins; ceramides such as stearyl and palmitoyl ceramides; glycosphingolipids; lanolin and lanolin alcohols; and combinations and mixtures thereof. In a preferred embodiment, liquid to be spray dried optionally includes one or more phospholipids, such as, for example, a phosphatidylcholine, phosphatidylethanolamine, phosphatidylglycerol, phosphatidylserine, phosphatidylinositol or a combination thereof. In one embodiment, the phospholipids are endogenous to the lung. Specific examples of phospholipids are shown in Table 1. Combinations of phospholipids can also be employed.

TABLE 1

Phospholipids

| | |
|---|---|
| Dilaurylolyphosphatidylcholine (C12;0) | DLPC |
| Dimyristoylphosphatidylcholine (C14;0) | DMPC |
| Dipalmitoylphosphatidylcholine (C16:0) | DPPC |
| Distearoylphosphatidylcholine (C18:0) | DSPC |
| Dioleoylphosphatidylcholine (C18:1) | DOPC |
| Dilaurylolylphosphatidyl-glycerol | DLPG |
| Dimyristoylphosphatidylglycerol | DMPG |
| Dipalmitoylphosphatidylglycerol | DPPG |
| Distearoylphosphatidylglycerol | DSPG |
| Dioleoylphosphatidylglycerol | DOPG |
| Dimyristoyl phosphatidic acid | DMPA |
| Dimyristoyl phosphatidic acid | DMPA |
| Dipalmitoyl phosphatidic acid | DPPA |
| Dipalmitoyl phosphatidic acid | DPPA |
| Dimyristoyl phosphatidylethanolamine | DMPE |
| Dipalmitoyl phosphatidylethanolamine | DPPE |
| Dimyristoyl phosphatidylserine | DMPS |
| Dipalmitoyl phosphatidylserine | DPPS |
| Dipalmitoyl sphingomyelin | DPSP |
| Distearoyl sphingomyelin | DSSP |

Charged phospholipids also can be employed to generate particles that contain nanoparticles comprising bioactive agents. Examples of charged phospholipids are described in U.S. patent application 20020052310.

In addition to lung surfactants, such as, for example, the phospholipids discussed above, suitable surfactants include but are not limited to cholesterol, fatty acids, fatty acid esters, sugars, hexadecanol; fatty alcohols such as polyethylene glycol (PEG); polyoxyethylene-9-lauryl ether; a surface active fatty acid such as palmitic acid or oleic acid; glycocholate; surfactin; a poloxamer; a sorbitan fatty acid ester such as sorbitan trioleate (Span 85), Tween 80 (Polyoxyethylene Sorbitan Monooleate); tyloxapol, polyvinyl alcohol (PVA), and combinations thereof. Methods of preparing and administering particles including surfactants, and, in particular phospholipids, are disclosed in U.S. Pat. No. 5,855,913 to Hanes et al. and in U.S. Pat. No. 5,985,309 to Edwards et al.

The particles can further comprise an amino acid, including but not limited to, leucine, isoleucine, alanine, valine, phenylalanine, glycine and tryptophan. Combinations of amino acids can also be employed. Suitable non-naturally occurring amino acids include, for example, beta-amino acids. Both D, L configurations and racemic mixtures of hydrophobic amino acids can be employed. Suitable amino acids can also include amino acid derivatives or analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1-C8 hydrocarbons which are completely saturated, which contain one or two heteroatoms such as nitrogen, oxygen or sulfur and/or which contain one or more units of unsaturation. Aromatic or aryl groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridinyl. A number of suitable amino acids, amino acids analogs and salts thereof can be obtained commercially. Others can be synthesized by methods known in the art. Synthetic techniques are described, for example, in Green and Wuts, "Protecting Groups in Organic Synthesis", John Wiley and Sons, Chapters 5 and 7, 1991.

The amino acid or salt thereof can be present in the particles in an amount from about 0% to about 60 weight %, preferably, from about 5 weight % to about 30 weight %. Methods of forming and delivering particles which include an amino acid are described in U.S. Pat. No. 6,586,008.

The spray dried particles can include nanoparticles containing one or more bioactive agents or other materials. Nanoparticles can be produced according to methods known in the art, for example, emulsion polymerization in a continuous aqueous phase, emulsion polymerization in a continuous organic phase, milling, precipitation, sublimation, interfacial polycondensation, spray drying, hot melt microencapsulation, phase separation techniques (solvent removal and solvent evaporation), nanoprecipitation as described by A. L. Le Roy Boehm, R. Zerrouk and H. Fessi (J. Microencapsulation, 2000, 17: 195-205) and phase inversion techniques. Additional methods for producing include evaporated precipitation, as described by Chen et al. (International Journal of Pharmaceutics, 2002, 24, pp 3-14) and the use of supercritical carbon dioxide as an anti-solvent (as described, for example, by J.-Y. Lee et al., Journal of Nanoparticle Research, 2002, 2, pp 53-59). Nanocapsules can be produced by the method of F. Dalencon, Y. Amjaud, C. Lafforgue, F. Derouin and H. Fessi (International Journal of Pharmaceutics., 1997, 153:127-130). U.S. Pat. Nos. 6,143,211, 6,117,454 and 5,962,566; Amnoury (J. Pharm. Sci., 1990, pp 763-767); Julienne et al., (Proceed. Intern. Symp. Control. Rel. Bioact. Mater., 1989, pp 77-78); Bazile et al. (Biomaterials 1992, pp 1093-1102); Gref et al. (Science 1994, 263, pp 1600-1603); Colloidal Drug Delivery Systems (edited by Jorg Kreuter, Marcel Dekker, Inc., New York, Basel, Hong Kong, pp 219-341); and WO 00/27363, describe the manufacture of nanoparticles and incorporation of bioactive agents, for example, drugs, in nanoparticles.

Intact (preformed) nanoparticle can be added to the solution(s) to be spray dried. Alternatively, reagents capable of forming nanoparticles during the mixing and/or spray drying process can be added to the solutions to be spray dried.

The excipient/carrier can be present in the particles in an amount ranging from about 5 weight percent (%) to about 95 weight %. Preferably, it can be present in the particles in an amount ranging from about 20 weight % to about 80 weight %.

Optionally the particles or aggregates are coated. Suitable coatings include proteins and surfactants. Coatings may be used to target to specific tissues or cells, or to increase bioadhesion. The particles or aggregates can also include other additives, for example, buffer salts.

II. Particle Delivery

Methods and Devices for Administration

Preferably, the bioactive agent is delivered to a target site, for example, a tissue, organ or entire body, preferably the lungs, in an effective amount. As used herein, the term "effective amount" means the amount needed to achieve the desired therapeutic or diagnostic effect or efficacy. The actual effective amounts of bioactive agent can vary according to the specific bioactive agent or combination thereof being utilized, the particular composition formulated, the mode of administration, and the age, weight, condition of the patient, and severity of the symptoms or condition being treated. Dosages for a particular patient can be determined by one of ordinary skill in the art using conventional considerations, e.g., by means of an appropriate, conventional pharmacological protocol. In one embodiment, the bioactive agent is coated onto the nanoparticle.

Although described primarily with reference to pulmonary administration, it is understood that the particles may be administered nasally, orally, vaginally, rectally, topically, or by injection.

The formulations are administered to a patient in need of treatment, prophylaxis or diagnosis. Administration of particles to the respiratory system can be by means such as known in the art. For example, particles (agglomerates) can be delivered from an inhalation device. In a preferred embodiment, particles are administered via a dry powder inhaler (DPI). Metered-dose-inhalers (MDI), nebulizers, or instillation techniques also can be employed. Preferably, delivery is to the alveoli region of the pulmonary system, the central airways, or the upper airways.

Various suitable devices and methods of inhalation which can be used to administer particles to a patient's respiratory tract are known in the art. For example, suitable inhalers are described in U.S. Pat. Nos. 4,995,385, and 4,069,819 to Valentini et al., U.S. Pat. No. 5,997,848 to Patton. Other examples include, but are not limited to, the Spinhaler® (Fisons, Loughborough, U.K.), Rotahaler® (Glaxo-Wellcome, Research Triangle Technology Park, N.C.), Flow-Caps® (Hovione, Loures, Portugal), Inhalator® (Boehringer-Ingelheim, Germany), the Aerolizer® (Novartis, Switzerland), the diskhaler (Glaxo-Wellcome, RTP, NC) and others, known to those skilled in the art. Preferably, the particles are administered as a dry powder via a dry powder inhaler. In one embodiment, the dry powder inhaler is a simple, breath actuated device. An example of a suitable inhaler which can be employed is described in U.S. Pat. No. 6,766,799.

A receptacle is used to enclose or store particles and/or respirable pharmaceutical compositions comprising the particles for subsequent administration. The receptacle is filled with the particles using methods as known in the art. For example, vacuum filling or tamping technologies may be used. Generally, filling the receptacle with the particles can be carried out by methods known in the art. In one embodiment, the particles that are enclosed or stored in a receptacle have a mass of at least about 5 milligrams up to about 100 milligrams. In another embodiment, the mass of the particles stored or enclosed in the receptacle comprises a mass of bioactive agent from at least about 1.5 mg to at least about 20 milligrams. In one embodiment, the volume of the inhaler receptacle is at least about 0.37 $cm^3$ to 0.95 $cm^3$. Alternatively, the receptacles can be capsules, for example, capsules designated with a particular capsule size, such as 2, 1, 0, 00 or 000. Suitable capsules can be obtained, for example, from Shionogi (Rockville, Md.). Blisters can be obtained, for example, from Hueck Foils, (Wall, N.J.). Other receptacles and other volumes thereof suitable for use in the instant invention are also known to those skilled in the art.

Preferably, particles administered to the respiratory tract travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. In a preferred embodiment, most of the mass of particles deposits in the deep lung. In another embodiment, delivery is primarily to the central airways. Delivery to the upper airways can also be obtained.

Aerosol dosage, formulations and delivery systems also may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313, 1990; and in Moren, "Aerosol dosage forms and formulations," in: Aerosols in Medicine. Principles, Diagnosis and Therapy, Moren et al., Eds, Elsevier, Amsterdam, 1985.

Bioactive agent release rates from particles can be described in terms of release constants. The first order release constant can be expressed using the following equations:

$$M_{(t)} = M_{(\infty)} * (1 - e^{-k*t}) \tag{1}$$

Where k is the first order release constant. $M_{(\infty)}$ is the total mass of bioactive agent in the bioactive agent delivery system, e.g. the dry powder, and $M_{(t)}$ is the amount of bioactive agent mass released from dry powders at time t.

Equation (1) may be expressed either in amount (i.e., mass) of bioactive agent released or concentration of bioactive agent released in a specified volume of release medium.

For example, Equation (1) may be expressed as:

$$C_{(t)} = C_{(\infty)} * (1 - e^{-k*t}) \text{ or Release}_{(t) = Release(-\infty)} * (1 - ee^{-k*t}) \tag{2}$$

Where k is the first order release constant. $C_{(\infty)}$ is the maximum theoretical concentration of bioactive agent in the release medium, and $C_{(t)}$ is the concentration of bioactive agent being released from dry powders to the release medium at time t.

Drug release rates in terms of first order release constant can be calculated using the following equations:

$$k = -\ln(M_{(\infty)} - M_{(t)})/M_{(\infty)}/t \tag{3}$$

Release rates of bioactive agents from particles can be controlled or optimized by adjusting the thermal properties or physical state transitions of the particles. The particles can be characterized by their matrix transition temperature. As used herein, the term "matrix transition temperature" refers to the temperature at which particles are transformed from glassy or rigid phase with less molecular mobility to a more amorphous, rubbery or molten state or fluid-like phase. As used herein, "matrix transition temperature" is the temperature at which the structural integrity of a particle is diminished in a manner which imparts faster release of bioactive agent from the particle. Above the matrix transition temperature, the particle structure changes so that mobility of the bioactive agent molecules increases resulting in faster release. In contrast, below the matrix transition temperature, the mobility of the bioactive agent particles is limited, resulting in a slower release. The "matrix transition temperature" can relate to different phase transition temperatures, for example, melting temperature ($T_m$), crystallization temperature ($T_c$) and glass transition temperature ($T_g$) which represent changes of order and/or molecular mobility within solids.

Experimentally, matrix transition temperatures can be determined by methods known in the art, in particular by differential scanning calorimetry (DSC). Other techniques to characterize the matrix transition behavior of particles or dry powders include synchrotron X-ray diffraction and freeze fracture electron microscopy.

As used herein, the term "nominal dose" means the total mass of bioactive agent which is present in the mass of particles targeted for administration and represents the maximum amount of bioactive agent available for administration.

Patients to be Treated; Effective Dosages

The formulations described herein are particularly suited to treatment of respiratory diseases such as TB, SARS, meningococcal meningitis, RSV, influenza, and small pox. In the preferred embodiment, the patients to be treated have chronic or long term infection, or drug resistant infection.

In the case of an antibiotic such as capreomycin, a dosage equivalent to a dosage in the range of 30-100 mg, more preferably 30-60 mg, given orally, is administered once or twice daily for fast release, and once a week for slow release. Leucine is the preferred excipient.

The present invention will be further understood by reference to the following non-limiting examples.

Example 1

Large Porous Particles Containing Capreomycin

Multi-drug resistant tuberculosis (MDR-TB) is emerging as a significant public health threat, creating an unmet medical need that requires the development of new treatment approaches. Direct, topical delivery of antibiotics to infected lungs is used to obtain the primary goal of targeting high drug doses to the site of primary infection for rapid sterilization of the lung mucosa and reduction in the duration of MDR-TB therapy.

Dry powder aerosols containing 50-80% capreomycin, that exhibit similar physical and aerosolization properties, have been made. Aerosols with geometric diameters ranging from 2-10 μm and aerodynamic diameters in the 5-6 μm range were formed by spray drying. Optimization of processing parameters increased powder yields up to 60% prior to large batch scale-up. The aerosols show excellent storage capacity at refrigerated, room temperature, and accelerated (40° C.) conditions, with both the chemical and physical properties remaining stable for up to 2 months of storage.

Experimental Methods

Preparation of Dry Powder Aerosols

Aerosols were prepared by heating an 80:20 capreomycin: leucine solution (36 g in 5000 mL of 50% ethanol) to 60° C. and spray drying the solution using a Niro spray dryer at a feed flowrate of 80 mL/min, an atomizer flowrate of 28-31 g/min and a process gas flowrate of 79-82 kg/hr. Inlet temperature was varied from 189-192° C. to achieve an outlet temperature of ~65° C.

In a second example, a solution containing 28.8 g capreomycin sulfate (Lilly, Control No. 7RT71R) and 7.2 g L-leucine (Sigma L-8912, Lot 044K0381) in 2500 mL Milli-Q water and 2500 mL of 200 proof ethanol (PharmCo 111ACS200, Batch 04259-14, Lot 0409144) was heated to 60° C. and spray dried using a Niro spray dryer at a feed flowrate of 80 mL/min, an atomizer flowrate of 28-31 g/min and a process gas flowrate of 79-82 kg/hr. Inlet temperature was varied from 189-192° C. to achieve an outlet temperature of ~65° C.

Yield: 17.5149 g=>48.7%

Physical Aerosol Characterization

Each spray-dried powder was initially characterized for morphology, geometric size, and aerosolization properties. Particle morphology was observed by scanning electron microscopy with a LEO 982 Field Emission Scanning Electron Microscope (SEM) (Zeiss). Particle size was measured by laser diffraction using a HELOS diffractometer and a RODOS variable-shearing dry powder disperser (Sympatec) at applied regulator pressures of 0.5, 1, 2, and 4 bar. The aerodynamic properties of the powders dispersed from an inhaler device were assessed with cascade impaction using gravimetric analysis via an 8-stage Mark II Andersen Cascade Impactor (ACI-8, Thermo Electron, Waltham, Mass.) to measure fine particle fraction of the total dose ($FPF_{TD}$). The $FPF_{TD}$ reported measures the fraction of aerosols with aerodynamic diameters less than 3.3 or 5.8 μm. An $FPF_{TD}$<3.3 μm represents the percentage of aerosols that should deposit in the lower respiratory tract, whereas an $FPF_{TD}$<5.8 μm represents the percentage of aerosols that should deposit in the middle to lower respiratory tract.

The bulk density of the particles was determined by tap density measurements. Briefly, particles were loaded into 0.3 ml sections of a 1-ml plastic pipette, capped with NMR tube caps, and tapped approximately 300-500 times until the volume of the powder did not change. The tap density was determined from the difference between the weight of the pipette before and after loading, divided by the volume of powder after tapping.

Chemical Aerosol Characterization

Capreomycin content in the powders was determined by HPLC. Capreomycin content in each powder was determined by HPLC analysis in 22:78 methanol:phosphate buffer with 0.3 wt % heptafluorobutyric acid using a C18 reverse-phase column (Agilent ZORBAX® Eclipse XDB-C18) at 1.0 mL/min and 25° C.

Stability Testing

The powder was aliquoted into 15 glass scintillation vials (~200 mg each) in a glove box at 10.5% RH, then tightly capped. 3 vials each were placed in 4 plastic desiccated chambers containing drierite. The chambers were stored at room temperature under dark conditions, at room temperature exposed to sunlight, at 4° C. (refrigerated), and at 40° C. and 75% RH in a humidity chamber as an accelerated stability condition. The final 3 vials were placed uncapped at 40° C. and 75% RH in a humidity chamber. Timepoints are 0, 1, 2 and 6 weeks, 2 months, and 3 months. At each timepoint, the powders' physical and chemical properties were characterized.

RESULTS AND DISCUSSION

Dry powder aerosols containing various percentages of capreomycin and leucine were formed by spray drying. The mass-mean diameter of each formulation, as determined using a HELOS/RODOS laser diffraction system at a regulator pressure of 1.0 bar, is shown in Table 2. No significant difference in diameter was seen with a change in regulator pressure. This suggests that aerosol flight characteristics for these powders are independent of a patient's inspiratory flowrate.

SEM images of dry powder aerosols containing 80% and 90% capreomycin demonstrate that as the percentage of capreomycin in the dry powder aerosols was increased up to 80%, a decrease in average diameter was seen (Table 2). At 90% capreomycin, an aerosol containing two diameters of spheres were observed by laser diffraction and SEM. This dual population led to an increase in average diameter of the powder.

$FPF_{TD}$ for the 50-80% capreomycin-containing aerosols were not significantly different. However, the 90% capreomycin aerosol showed about a 30% decrease in $FPF_{TD}$. Since aerosols containing the largest amount of capreomycin possible, but with good flight properties, is needed, 80% capreomycin-containing aerosols were used for further studies.

TABLE 2

Average size and FPF$_{TD}$ of capreomycin-containing dry powder aerosols

| Formulation (capreo:leucine) | Diameter (μm) (1.0 bar) | FPF$_{TD}$ < 5.8 um (%) |
|---|---|---|
| 50:50 | 4.2 | 68.8 ± 1.3 |
| 60:40 | 3.7 | 65.3 ± 1.4 |
| 70:30 | 3.4 | 69.1 ± 2.0 |
| 80:20 | 3.0 | 66.1 ± 1.0 |
| 90:10 | 3.3 | 40.4 ± 1.5 |

Initial scale-up of powder production resulted in a 48.7% yield. These aerosols, used for stability and pharmacokinetic studies, had an average geometric diameter of 4.2 μm, with an aerodynamic diameter range of 4-6 microns. A geometric standard deviation (GSD) of 1.8 μm was determined from W. C. Hinds. Aerosol Technology. John Wiley & Sons, Inc., New York, 1999:

$$GSD = (d_{84\%}/d_{16\%})^{0.5} \qquad \text{eqn. (1)}$$

where $d_n$ is the diameter at the $n^{th}$ percentile of the cumulative distribution, and showed that the aerosol was nearly monodisperse.

No significant difference in diameter was seen with a change in regulator pressure. This suggests that aerosol flight characteristics for these powders are independent of a patient's inspiratory flowrate.

The resulting particles had high drug loadings. Repeated spray drying on different days showed good reproducibility with respect to particle size and morphology. Gross visual stability tests at 4° C., room temperature and 40° C. showed no size or morphology changes after 2 and one-half weeks.

The FPF$_{TD}$ of aerosols stored at 40° C. for 6 weeks decreased by 40%. However, the FPF$_{TD}$ under other storage conditions remained stable for up to 2 months.

The content of capreomycin in formulations stored in closed vials at 4° C., RT, and 40° C. remained stable for up to three months. When placed in direct contact with a 40° C. and 75% RH atmosphere, the aerosols adsorbed significant amounts of water, leading to a decrease in capreomycin content per mass of aerosol.

Figure 1B:
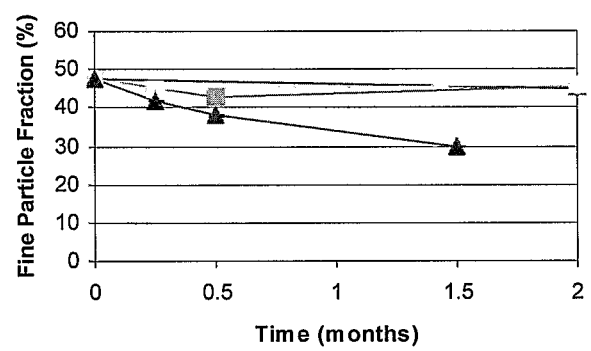
Figure 1C:
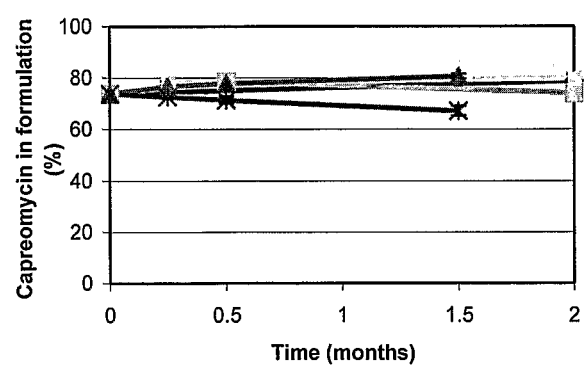

A three month physical and chemical stability analysis of the 80% capreomycin-containing aerosols was conducted under refrigerated (4° C.), room temperature (RT, approximately 25° C.), and accelerated (40° C.) conditions. FIGS. 1A, 1B, and 1C show the stability of the aerosol geometric diameter, fine particle fraction (FPF$_{TD}$), and chemical content over time.

No significant change was seen in the geometric diameter under all conditions (FIG. 1A). The FPF$_{TD}$ of aerosols stored at 40° C. for 6 weeks decreased by 40% (FIG. 1B). However, the FPF$_{TD}$ under other storage conditions remained stable for up to 3 months. The content of capreomycin in formulations stored in closed vials at 4° C., RT, and 40° C. remained stable for up to 3 months (FIG. 1C). When placed in direct contact with a 40° C. and 75% RH atmosphere, the aerosols adsorbed significant amounts of water, leading to a decrease in capreomycin content per mass of aerosol.

In summary, an injectable hydrophilic TB drug molecule, capreomycin, was formulated into a dry powder aerosol form for inhalation. Due to the large doses of antibiotics required for treatment, a dry powder aerosol with high drug loading (80% capreomycin) that exhibits excellent aerosolization properties (FPF$_{TD}$<5.8 μm of 48%) was prepared. No significant difference in geometric diameter was seen with a change in applied regulator pressure, suggesting that aerosol flight characteristics for these powders are independent of a patient's inspiratory flowrate. Significantly, these aerosols show excellent storage capacity at refrigerated, room temperature, and accelerated (40° C.) conditions, with both the chemical and physical properties remaining stable for up to three months of storage.

It is understood that the disclosed invention is not limited to the particular methodology, protocols, and reagents described as these may vary. It is also to be understood that the terminology used herein is for the purpose of describing particular embodiments only, and is not intended to limit the scope which will be limited only by the appended claims.

We claim:

1. A dry powder formulation for deposition in the middle to lower respiratory tract for treatment of a respiratory infection comprising
   microparticles containing at least 50% by weight of capreomycin and leucine,
   wherein the capreomycin and leucine are in a ratio of 80:20,
   wherein the microparticles have a diameter between one and 30 microns and a volume median geometric diameter of at least about 5 microns to about 15 microns, and have a fine particle fraction of the total dose (FPF$_{TD}$) less than 5.8 μm from about 40% to 70%.

2. The formulation of claim 1 comprising microparticles containing 50 to 80% capreomycin.

3. The formulation of claim 2 wherein the microparticles have an aerodynamic diameter of between 5 and 6 microns.

4. The formulation of claim 1 in a capsule for pulmonary delivery.

5. The formulation of claim 1 in a dosage unit wherein capreomycin is included in an effective amount for treatment of a disease selected from the group consisting of tuberculosis, severe acute respiratory syndrome (SARS), meningococcal meningitis, respiratory syncytial virus (RSV), influenza, and small pox.

6. The formulation of claim 1 in a dosage unit for treatment of a chrome or drug resistant respiratory infection.

7. The formulation of claim 5 in a dosage unit for treatment of tuberculosis.

8. The formulation of claim 7 wherein the tuberculosis is multi-drug resistant.

9. The formulation of claim 1 wherein capreomycin is in a loading of greater than 60% by weight.

10. The formulation of claim 1 wherein the microparticles have a range of an aerodynamic diameter of between four and six microns.

11. A method of treatment comprising administering to a patient an effective amount of the formulation of claim 1.

12. The method of claim 11 wherein the formulation is administered once or twice a day and is a fast release formulation.

13. The method of claim 11 wherein the formulation is administered once a week and is a slow release formulation.

14. The method of claim 11 wherein the formulation is administered to a person in need thereof at a dosage equivalent to 30 to 100 mg of capreomycin delivered orally.

* * * * *